Nov. 18, 1958 A. NILL Plant Pat. 1,772
AZALEA PLANT
Filed April 4, 1958
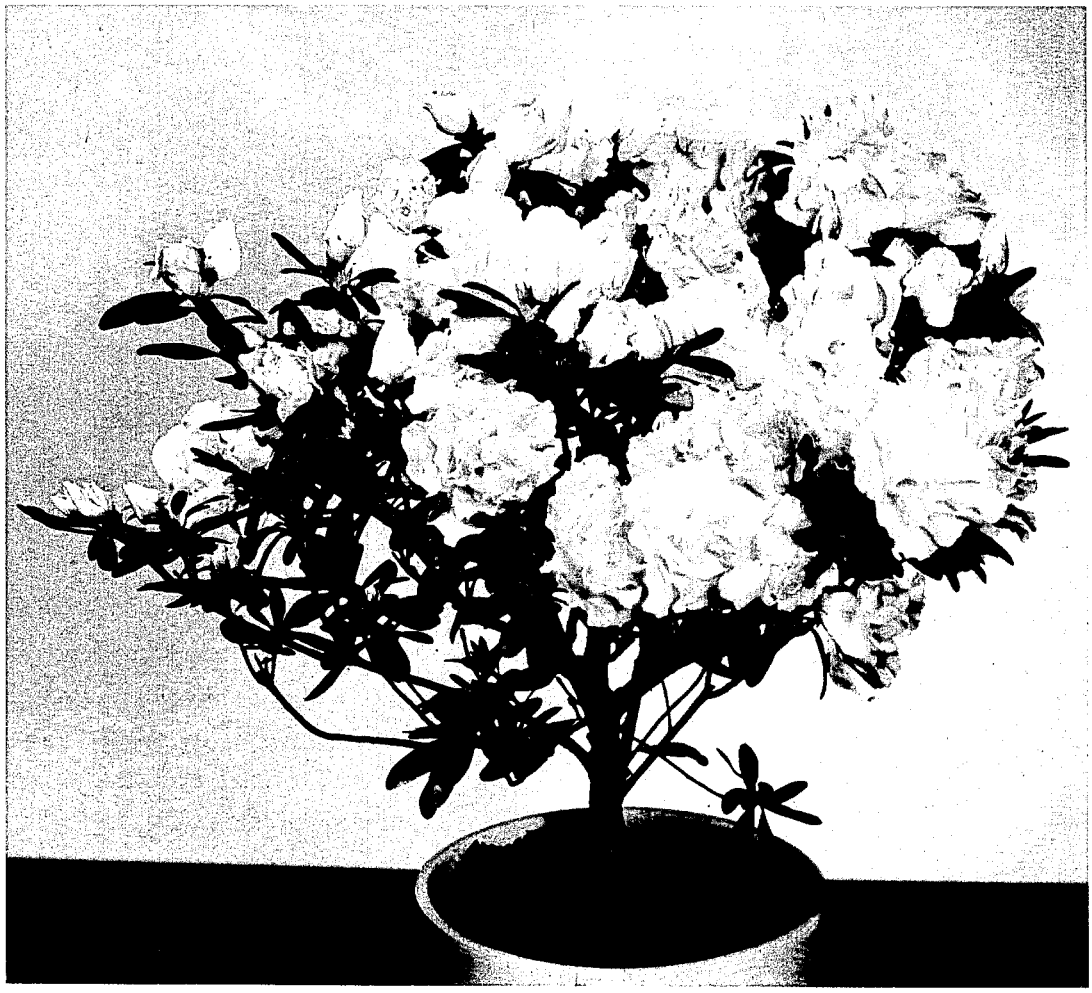
INVENTOR
Alfred Nill
BY Robert Cobb
ATTORNEYS United States Patent Office Plant Pat. 1,772
Patented Nov. 18, 1958

1,772

AZALEA PLANT

Alfred Nill, Wantagh, N. Y., assignor to Dauernheim, Inc., Wantagh, N. Y., a corporation of New York Application April 4, 1958, Serial No. 726,595

1 Claim. (Cl. 47—60)

The present invention relates to a new and distinct variety of azalea plant of the Indica or Indian type, which was discovered by me as a sport of the variety "Jean Haarens" (unpatented). At the time of my initial discovery of this sport, I was growing a block of azaleas in a greenhouse on the property of the nursery of the assignee of this application at Wantagh, Long Island, New York. In this block of plants, my attention was attracted to one particular plant because of the distinctive color and other characteristics of the flowers which appeared to be quite different from those of the other plants, as well as from any other azalea with which I was familiar. On closer examination of the plant, I found that one of the plants of the variety "Jean Haarens" had sported, and I thereupon immediately took steps to preserve the sport, keep it under observation, and later to asexually reproduce the same. These continued observations and asexual reproductions, as performed by both grafting and cuttings at Wantagh, Long Island, New York, showed that the sport was definitely different from its parent and from all other varieties of which I was aware, while apparently still falling in the general class of Indian azaleas (var. *R. indicum*) of the Belgian type.

While the new variety is generally similar in form and habit of growth to its parent, it is particularly characterized as to novelty by a unique combination of outstanding features which include the following:

(1) Vigorous and uniform habits of growth;

(2) Persistent foliage;

(3) Firm texture and attendant good keeping quality of the flowers;

(4) A distinctive pink general color tonality of the flowers; and (5) Excellent suitability for forcing.

The accompanying drawing shows a typical specimen plant of my new variety as depicted in color as nearly true as it is reasonably possible to make the same in a color illustration of this character.

The following is a detailed description of the new variety, with color terminology in accordance with Ridgway's Color Standards and Nomenclature, except where general color terms of ordinary dictionary significance are obvious:

(Observations made from specimens grown in a greenhouse at Wantagh, Long Island, New York.)

Propagation: Holds its distinguishing characteristics through succeeding propagations by grafting and cuttings; is particularly good for own-rooting; excellent for forcing.

Growth: Vigorous; similar in form and vigor to parent "Jean Haarens."

Blooming habit: Even; blooms earlier than parent variety by from 3 to 4 weeks; usually blooms from about February 1st to about April 15th.

Foliage: Persists; holds better than most indicum varieties.

*Size (mature).*—Length—from about 1¾ inches to 2 inches. Width—from about ½ inch to ⅝ inch.

*Shape.*—Fairly eliptical; some minor variations; some with pointed tips; some with tendency to curl at tips during dormancy, giving a cupped effect which disappears during forcing.

*Quantity.*—Normal.

*Texture.*—Quite similar to most varieties of the indicum type; not as smooth and glossy as the variety Indica Verveanana (unpatented) or the Kurume variety "Snow" (unpatented).

*Margin.*—Smooth.

*Color.*—Old foliage: upper side—Dark Dull Yellow-Green, Plate XXXII; under side—Chromium Green, Plate XXXII. New foliage: upper side—Spinach Green, Plate V; under side—Lettuce Green, Plate V.

Flowers:

*Borne.*—Usually 2 flowers per bud sheath.

*Quantity.*—Not as free-flowering as parent or other indicum varieties, but still good quantity.

*Continuity.*—One crop per season.

*Size.*—Approximately 3 inches in diameter.

Petalage:

*Female flower.*—Hose-in-hose; the back petal is 5-pointed; the center has 10 points, but is wavy, curled, irregularly shaped and clustered, giving the appearance of considerable doubleness.

*Male flower.*—Hose-in-hose. Outer petals—5-pointed. Inner petals—10-pointed and uniformly shaped, giving the appearance of doubleness and appearing like 15 petals.

*Texture.*—Firm; harder than most indicum varieties.

*Color.*—Geranium Pink, Plate I, shading through La France Pink, Plate I to white; both male and female flowers have a touch of yellow near the centers, and in the male flower, this is rather delicate and quite pleasing; in the female flower, this is not apparent without dissecting the flower due to the clustered formation of the center tier of petalage.

Bud:

*Form.*—Pointed.

*Color.*—Similar to open flowers, but somewhat deeper color.

Reproductive organs:

*Female flower.*—Has styles about 1½ inches long of pink color, with Chartreuse stigma.

*Male flower.*—Few reproductive organs; stamens have one or more pink anthers with Chartreuse pollen; unlike some azaleas, pollen does not detract from appearance of flower when the flower is open, as stamens are shorter than styles, and are relatively insignificant; pollen holds its color quite well.

I claim:

A new and distinct variety of azalea plant of the Belgian Indicum type, substantially as herein shown and described, characterized particularly as to novelty by the unique combination of vigorous and uniform habits of growth, persistent foliage, firm texture and attendant good keeping quality of the flowers, a distinctive pink general color tonality of the flowers, and excellent suitability for forcing.

No references cited.